United States Patent [19]
Schwalge et al.

[11] Patent Number: 5,912,249
[45] Date of Patent: Jun. 15, 1999

[54] FUNGICIDAL MIXTURES

[75] Inventors: Barbara Schwalge, Heidelberg; Ruth Müller, Friedelsheim; Herbert Bayer; Hubert Sauter, both of Mannheim; Reinhold Saur, Böhl-Iggelheim; Klaus Schelberger, Gönnheim; Eberhard Ammermann, Heppenheim; Gisela Lorenz, Hambach; Siegfried Strathmann, Limburgerhof, all of Germany

[73] Assignee: BASF Aktiengesellschaft, Ludwigshafen, Germany

[21] Appl. No.: 09/000,181

[22] PCT Filed: Aug. 1, 1996

[86] PCT No.: PCT/EP96/03386

§ 371 Date: Jan. 20, 1998

§ 102(e) Date: Jan. 20, 1998

[87] PCT Pub. No.: WO97/06680

PCT Pub. Date: Feb. 27, 1997

[30] Foreign Application Priority Data

Aug. 17, 1995 [DE] Germany .................. 195 30 170

[51] Int. Cl.$^6$ .......................... A01N 37/18; A01N 43/54
[52] U.S. Cl. ........................................ 514/256; 514/619
[58] Field of Search ........................... 514/256, 619

[56] References Cited

U.S. PATENT DOCUMENTS 5,464,839  11/1995  Wingert et al. ................... 514/256

FOREIGN PATENT DOCUMENTS

| 1 217 623 | 1/1971 | United Kingdom . |
| 2 279 568 | 1/1995 | United Kingdom . |
| 95/18789 | 7/1995 | WIPO . |
| 85/21154 | 8/1995 | WIPO . |

OTHER PUBLICATIONS

Res. Discl. 1992, Jun., No. 338 9 pages.
Pesticide Sc., vol. 44, No. 1, May 1995, pp. 77–79.
CROPU, Derwent Abst. 95–81855 1995.
CROPU, Derwent Abst. 95–81869 1995.

Primary Examiner—Allen J. Robinson
Attorney, Agent, or Firm—Keil & Weinkauf

[57] ABSTRACT

Fungicidal mixture comprising a) an oxime ether carboxamide of the formula I

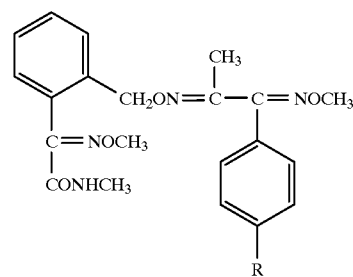

where R is hydrogen or halogen and b) (±)-(2-chlorophenyl)(4-chlorophenyl)(pyrimidin-5-yl) methanol

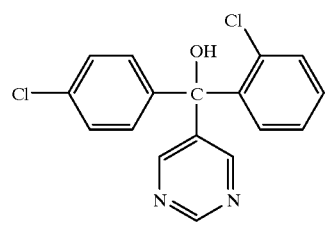

in a synergistically active amount.

6 Claims, No Drawings

FUNGICIDAL MIXTURES

This application is a 371 of PCT/EP96/03386 filed Aug. 1, 1996.

The present invention relates to a fungicidal mixture which comprises a) an oxime ether carboxamide of the formula I

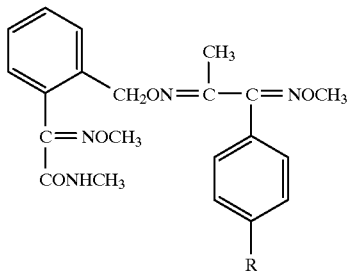

where R is hydrogen or halogen and b) (±)-(2-chlorophenyl)(4-chlorophenyl)(pyrimidin-5-yl)methanol

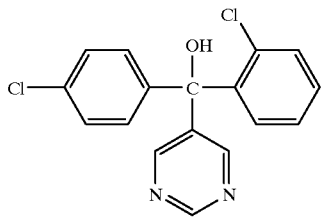

in a synergistically active amount.

Moreover, the invention relates to methods of controlling harmful fungi using mixtures of the compounds I and II and to the use of the compound I and the compound II for the preparation of such mixtures.

The compounds of the formula I, their preparation and their action against harmful fungi are disclosed in the literature (WO-A 95/18,789). Also disclosed is the compound II (GB-A 1,218,623; common name: fenarimol), its preparation and its action against harmful fungi.

It was an object of the present inventions [sic] to provide mixtures which have an improved action against harmful fungi combined with a reduced total amount of active ingredients applied (synergistic mixtures) with a view to reducing the application rate and to improving the spectrum of action of the known compounds.

Accordingly, we have found that this object is achieved by the mixtures defined at the outset. Moreover, we have found that better control of the harmful fungi is possible by applying the compound I and the compounds [sic] II simultaneously together or separately or by applying the compound I and the compound II in succession than when the individual compounds are used.

In relation to the C=N double bond, the compounds of the formula I can be present in the E or the Z configuration (in relation to the group [sic] carboxylic acid function). Accordingly, they can be used in the mixture according to the invention in the form of the pure E or Z isomers or else in the form of an E/Z isomer mixture. The E/Z isomer mixture or the E isomer are preferably used in each case, the E isomer of the compound I being particularly preferred.

R in formula I is hydrogen or a halogen atom such as fluorine, chlorine, bromine or iodine, especially hydrogen, fluorine or chlorine, in particular hydrogen or fluorine.

Due to the basic character of the NH or OH gorup, the compounds I and the compound II are capable of forming salts or adducts with inorganic or organic acids or with metal ions.

The C=N double bonds of the oxime ether groups in the side chain of the compounds I can exist in each case in the form of pure E or Z isomers or as E/Z isomer mixtures. The compounds I can be used in the mixtures according to the invention as isomer mixtures or else as the pure isomers. With a view to their use, compounds I which are particularly preferred are those where both oxime ether groups in the side chain are in the E configuration (E/E).

Examples of inorganic acids are hydrohalic acids such as hydrofluoric acid, hydrochloric acid, hydrobromic acid and hydriodic acid, sulfuric acid, phosphoric acid and nitric acid.

Suitable organic acids are, for example, formic acid, carbonic acid and alkanoic acids such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, alkylsulfonic acids (sulfonic acids having straight-chain or branched alkyl radicals of 1 to 20 carbon atoms), arylsulfonic acids or aryldisulfonic acids (aromatic radicals such as phenyl and naphthyl which have attached to them one or two sulfo groups), alkylphosphonic acids (phosphonic acids having straight-chain or branched alkyl radicals of 1 to 20 carbon atoms), arylphosphonic acids or aryldiphosphonic acids (aromatic radicals such as phenyl and naphthyl which have attached to them one or two phosphoric acid radicals), it being possible for the alkyl or aryl radicals to have attached to them further substituents, eg. p-toluenesulfonic acid, salicylic acid, p-aminosalicylic acid, 2-phenoxybenzoic acid, 2-acetoxybenzoic acid etc.

Suitable metal ions are, in particular, the ions of the elements of the second main group, in particular calcium and magnesium, and of the third and fourth main group, in particular aluminum, tin and lead, and of the first to eighth subgroup, in particular chromium, manganese, iron, cobalt, nickel, copper, zinc and others. Especially preferred are the metal ions of the elements of the subgroups of the fourth period. The metals can exist in the various valencies which they can assume.

When preparing the mixtures, it is preferred to employ the pure active ingredients I and II, with which further active ingredients against harmful fungi or other pests such as insects, arachnids or nematodes, or else herbicidal or growth-regulating active ingredients or fertilizers can be admixed if required.

The mixtures of the compounds I and II, or the simultaneous joint or separate use of the compounds I and II, have an outstanding action against a wide spectrum of phytopathogenic fungi, in particular from the classes of the Ascomycetes and. Basidiomycetes. Some of them act systemically and can therefore be employed as foliar- and soil-acting fungicides.

They are especially important for controlling a large number of fungi in a variety of crop plants, such as cotton, vegetable species (eg. cucumbers, beans and cucurbits), barley, grass, oats, coffee, corn, fruit species, rice, rye, soy bean, grape vine, wheat, ornamentals, sugar cane and a large number of seeds.

They are particularly suitable for controlling the following phytopathogenic fungi: Erysiphe graminis (powdery mildew) in cereals, Erysiphe cichoracearum and Sphaerotheca fuliginea in cucurbits, Podosphaera leucotricha in apples, Uncinula necator in grape vines, Puccinia species in cereals, Rhizoctonia species in cotton, rice and lawns, Ustilago species in cereals and sugar cane, Venturia inaequalis (scab) in apples, Helminthosporium species in cereals, Rhynosporium Secalis [sic], Septoria nodorum in wheat, Botrytis cinera [sic] (gray mold) in strawberries and grape vines, Cercospora arachidicola in groundnuts, Pseudocercosporella herpotrichoides in wheat and barley, Pyricularia oryzae in rice, Phytophthora infestans in potatoes and tomatoes, Plasmopara viticola in grape vines, Alternaria species in vegetables and fruit, and Fusarium and Verticillium species.

Furthermore, they can be used in the protection of materials (eg. in the protection of wood), for example against Paecilomyces variotii.

The compounds I and II can be applied simultaneously together or separately or in succession, the order, in the case of separate application, generally not having any effect on the result of the control measures.

The compounds I and II are normally used in a weight ratio of 10:1 to 0.1:1, preferably 5:1 to 0.2:1, in particular 3:1 to 0.3:1.

The application rates of the mixtures according to the invention are from 0.01 to 3 kg/ha, preferably 0.01 to 1.5 kg/ha, in particular 0.01 to 0.5 kg/ha, depending on the nature of the desired effect. In the case of the compounds I, the application rates are from 0.005 to 0.5 kg/ha, preferably 0.005 to 0.5 kg/ha, in particular 0.005 to 0.3 kg/ha. Correspondingly, the application rates in the case of the compound II are from 0.005 to 0.5 kg/ha, preferably 0.01 to 0.5 kg/ha, in particular 0.01 to 0.3 kg/ha.

For seed treatment, the application rates of the mixture are generally from 0.001 to 10 g/kg of seed, preferably 0.01 to 10 g/kg, in particular 0.01 to 8 g/kg.

If phytopathogenic harmful fungi are to be controlled, the separate or joint application of the compounds I and II or of the mixtures of the compounds I and II is effected by spraying or dusting the seeds, the plants or the soils before or after sowing of the plants, or before or after plant emergence.

The fungicidal synergistic mixtures according to the invention, or the compounds I and II, can be formulated for example in the form of ready-to-spray solutions, powders and suspensions or in the form of highly concentrated aqueous, oily or other suspensions, dispersions, emulsions, oil dispersions, pastes, dusts, materials for spreading or granules, and be applied by spraying, atomizing, dusting, spreading or pouring. The use form depends on the intended purpose; in every case it should guarantee that distribution of the mixture according to the invention is as fine and uniform as possible.

The formulations are prepared in a manner known per se, eg. by adding solvents and/or carriers. It is usual to admix inert additives such as emulsifiers or dispersants with the formulations.

Suitable surfactants are the alkali metal salts, alkaline earth metal salts and ammonium salts of aromatic sulfonic acids, eg. ligno—, phenol—, naphthalene— and dibutyl-naphthalenesulfonic acid, and of fatty acids, alkyl— and alkylarylsulfonates, alkyl, lauryl ether and fatty alcohol sulfates, and salts of sulfated hexa— hepta— and octadecanols, or of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl—, octyl— or nonylphenol, alkylphenol polyglycol ethers, tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene [sic], lauryl alcohol polyglycol ether acetate, sorbitol esters, lignosulfite waste liquors or methylcellulose.

Powders, materials for spreading and dusts can be prepared by mixing or jointly grinding the compounds I or II or the mixture of the compounds I and II with a solid carrier.

Granules (eg. coated granules, impregnated granules or homogeneous granules) are usually prepared by binding the active ingredient, or active ingredients, to a solid carrier.

Fillers or solid carriers are, for example, mineral earths, such as silica gel, silicas, silica gels [sic], silicates, talc, kaolin, limestone, lime, chalk, bole, loess, clay, dolomite, diatomaceous earth, calcium sulfate, magnesium sulfate, magnesium oxide, ground synthetic materials, and fertilizers, such as ammonium sulfate, ammonium phosphate, ammonium nitrate, ureas, and products of vegetable origin, such as cereal meal, tree bark meal, wood meal and nutshell meal, cellulose powders or other solid carriers.

The formulations generally comprise 0.1 to 95% by weight, preferably 0.5 to 90% by weight, of one of the compounds I or II or of the mixture of the compounds I and II. The active ingredients are employed in a purity of from 90% to 100%, preferably 95% to 100% (according to NMR or HPLC spectrum [sic]).

The compounds I or II, or the mixtures, or the corresponding formulations, are applied by treating the harmful fungi or the plants, seeds, soils, areas, materials or spaces to be kept free from them with a fungicidally active amount of the mixture, or of the compounds I and II in the case of separate application. Application can be effected before or after infection by the harmful fungi.

Examples of the synergistic action of the mixtures according to the invention against harmful fungi.

The fungicidal action of the compounds and of the mixtures was demonstrated by the following experiments:

The active ingredients, separately or together, were formulated as a 10% emulsion in a mixture of 70% by weight of cyclohexanone, 20% by weight of Nekanil® LN (Lutensol® AP6, wetting agent having emulsifying and dispersing action, based on ethoxylated alkylphenols) and 10% by weight of Emulphor® EL (Emulan® EL, emulsifier based on ethoxylated fatty alcohols) and diluted with water to give the desired concentration.

Evaluation was by determining the infected leaf areas in percent. These percentages were converted into efficacies. The expected efficacies of the mixtures of the active ingredients were determined using Colby's formula [R.S. Colby, Weeds 15, 20–22 (1967)] and compared with the observed efficacies.

Colby's formula:

$$E = x + y - x \cdot y / 100$$

E expected efficacy, expressed in % of the untreated control, when using the mixture of the active ingredients A and B in the concentrations a and b x efficacy, expressed in % of the untreated control, when using active ingredient A in concentration a y efficacy, expressed in % of the untreated control, when using active ingredient B in concentration b The efficacy (E) was calculated as follows using Abbot's formula:

$$E = (1-\alpha) \cdot 100/\beta$$

α corresponds to the fungal infection of the treated plants in % and

β corresponds to the fungal infection of the untreated (control) plants in %

An efficacy of 0 means that the infection level of the treated plants corresponds to that of the untreated control plants; an efficacy of 100 means that the treated plants were not infected.

The expected efficacies of the mixtures of the active ingredients were calculated using Colby's formula and compared with the observed efficacies.

Activity against *Puccinia recondita* (brown rust of wheat)

Leaves of wheat seedlings (cultivar "Kanzler") were dusted with spores of brown rust (*Puccinia recondita*). The plants treated in this way were incubated for 24 h at 20–22° C. and a relative atmospheric humidity of 90–95% and then treated with the aqueous active ingredient preparation. After a further 8 days at 20–22° C. and 65–70% relative atmospheric humidity, the extent of fungal development was determined. Assessment was carried out visually.

| Active ingredient | Rate of application (ppm) | Efficacy [%] |
|---|---|---|
| untreated | -/- | 0 |
| I.a (R = H) | 8 | 0 |
|  | 4 | 0 |
| I.b (R = F) | 8 | 9 |
|  | 4 | 9 |
|  | 2 | 9 |
| II | 8 | 0 |
|  | 4 | 0 |
|  | 2 | 0 |

| Active ingredients | Rate of application/ mixing ratio | Efficacy Observed | Calculated |
|---|---|---|---|
| I.a + II | 8 + 8/1:1 | 61 | 0 |
|  | 8 + 8/1:1 | 35 | 0 |
| I.b + II | 8 + 8/1:1 | 87 | 9 |
|  | 4 + 4/1:1 | 80 | 9 |
|  | 2 + 2/1:1 | 48 | 9 |

We claim:

1. A fungicidal composition comprising
   a) an oxime ether carboxamide compound of the formula I

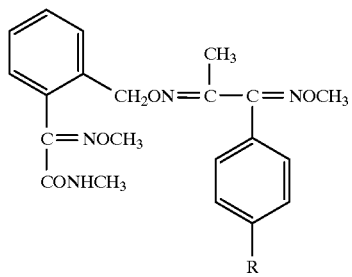

(I)

where R is hydrogen or halogen, and
   b) (±)-(2-chlorophenyl)(4-chlorophenyl)(pyrimidin-5-yl)-metha-nol of the formula II

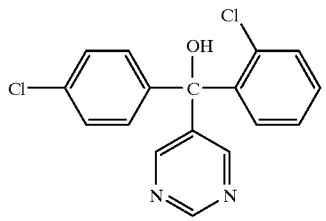

(II)

in a synergistically active amount.

2. The fungicidal composition defined in claim 1, wherein the weight ratio of the compound of the formula I to the compound of the formula II is 10:1 to 0.1:1.

3. A method of controlling harmful fungi, which comprises treating the harmful fungi, their environment, or the plants, seeds, soils, areas, materials or spaces to be kept free from said fungi with a synergistically effective amount of the compound of the formula I as defined in claim 1 and the compound of the formula II as defined in claim 1.

4. The method defined in claim 3, wherein the compound of the formula I and the compound of the formula II are applied simultaneously separately, or in succession.

5. The method defined in claim 3, wherein from 0.005 to 0.5 kg/ha of the compound of the formula I is applied.

6. The method defined in claim 3, wherein from 0.05 to 0.5 kg/ha of the compound of the formula II is applied.

* * * * *